US006285901B1

(12) United States Patent
Taicher et al.

(10) Patent No.: US 6,285,901 B1
(45) Date of Patent: Sep. 4, 2001

(54) QUANTITATIVE MAGNETIC RESONANCE METHOD AND APPARATUS FOR BONE ANALYSIS

(75) Inventors: Gersh Zvi Taicher; Arcady Reiderman, both of Houston, TX (US)

(73) Assignee: Echo Medical Systems, L.L.C., Houston, TX (US)

( * ) Notice: Subject to any disclaimer, the term of this patent is extended or adjusted under 35 U.S.C. 154(b) by 0 days.

(21) Appl. No.: 09/383,005

(22) Filed: Aug. 25, 1999

(51) Int. Cl.⁷ ........................................................ A61B 5/05
(52) U.S. Cl. .......................................... 600/410; 324/309
(58) Field of Search .............................. 324/309; 600/410

(56) References Cited

U.S. PATENT DOCUMENTS

| | | |
|---|---|---|
| 4,442,404 | 4/1984 | Bergmann . |
| 4,510,450 | 4/1985 | Brown . |
| 4,635,643 | 1/1987 | Brown . |

(List continued on next page.)

OTHER PUBLICATIONS

National Osteoporosis Foundation, "First guidelines for osteoporosis issues by National Osteoporosis Foundation in collaboration with multidisciplinary physician organizations", (news release Nov. 5, 1998).
Johnston et al., "Bone density measurement and the management of osteoporosis", Primer on Metabolic Bone Diseases and Disorders of Mineral Metabolism, pp. 93–100 (1996).
Majumdar et al., "A Review of the Recent Advances in Magnetic Resonance Imaging in the Assessment of Osteoporosis", Osteoporosis International (1995), 5:79–92.
Brochure from Bone Measurement Institute entitled "An Overview of Bone Mass Measurement Technology", no date printed.
Kuhn, "NMR Microscopy—Fundamentals, Limits and Possible Applications", Angewandte Chemie, International Edition in English, vol. 29, No. 1, Jan. 1990, pp. 1–19.
Genant et al., "Review—Noninvasive Assessment of Bone Mineral and Structure: State of the Art", Journal of Bone and Mineral Research, vol. 11, No. 6, 1996.

*Primary Examiner*—Christine Oda
*Assistant Examiner*—Dixomara Vargas
(74) *Attorney, Agent, or Firm*—Rosenthal & Osha L.L.P.

(57) ABSTRACT

A method for analyzing a bone is disclosed, including measuring a nuclear magnetic resonance signal corresponding to an amount of hydrogen within a known volume of the bone. The volume is large enough that so the signal corresponds to bulk properties within the volume. A bone matrix volume is determined from the signal. In one embodiment, the signal is a steady state free precession amplitude. The selected known volume in one example is selected by a sensitive point technique which includes imparting a substantially homogeneous static magnetic field to the bone and superimposing thereon mutually orthogonal oscillating gradient magnetic fields. In another example, the signal amplitude can be used to directly calculate bone mineral density of the bone. An apparatus according to one example of the invention includes a receptacle adapted to receive the foot and to substantially immobilize the foot, a magnet for inducing a static magnetic field within the calcaneus bone, a radio frequency pulse generator and an antenna coupled thereto positioned to induce a radio frequency magnetic field in the calcaneus bone to excite nuclear magnetic resonance therein, a receiver and an antenna coupled thereto to detect nuclear magnetic resonance signals originating in the calcaneus bone, means for localizing generation and detection of the nuclear magnetic resonance signals from within a selected known volume within the calcaneus bone, and means for calculating a property of specific bone tissue within the calcaneus bone from the nuclear magnetic resonance measurements.

35 Claims, 8 Drawing Sheets

U.S. PATENT DOCUMENTS

| | | |
|---|---|---|
| 4,701,705 | 10/1987 | Rollwitz . |
| 4,850,372 | 7/1989 | Ko et al. . |
| 4,880,007 | 11/1989 | Sadler et al. . |
| 5,126,674 | 6/1992 | Miller et al. . |
| 5,247,934 | 9/1993 | Wehrli et al. . |
| 5,270,651 | 12/1993 | Wehrli . |
| 5,539,309 | 7/1996 | Van Wyk et al. . |
| 5,593,659 | 1/1997 | Winchell et al. . |
| 5,596,274 | 1/1997 | Sezginer . |
| 5,672,968 | 9/1997 | Miller et al. . |
| 5,739,688 | 4/1998 | Krieg . |
| 5,818,228 | 10/1998 | Menon et al. . |
| 5,838,155 | 11/1998 | Bowers . |
| 6,185,444 * | 2/2001 | Ackerman et al. .................. 324/309 |

* cited by examiner

QUANTITATIVE MAGNETIC RESONANCE METHOD AND APPARATUS FOR BONE ANALYSIS

BACKGROUND OF THE INVENTION

1. Field of the Invention

The invention is related to the field of Nuclear Magnetic Resonance (NMR) and Magnetic Resonance Imaging (MRI) apparatus and methods. More specifically, the invention relates to methods and apparatus for using NMR for rapid, in-vivo determination of bone properties, such as Bone Mineral Density (BMD). The invention more particularly relates to NMR methods and apparatus for diagnosing diseases that affect bone, such as osteoporosis. In addition, the invention relates to methods and techniques of monitoring bone condition during progress of the disease, including the effect of different types of treatments on the disease.

2. Description of the Related Art

The description of the invention and its background are approached in the context of osteoporosis because osteoporosis is recognized as a significant public health problem, and NMR as well as other diagnostic techniques for bone studies have been widely applied and investigated. It is to be explicitly understood that the invention is not limited to the field of study, analysis and monitoring of osteoporosis.

a. Bone in a Human Skeleton

The skeleton serves to support the body, anchor muscles and protect vital organs. The human skeleton consists of approximately 80% of cortical (compact) bone and approximately 20% of trabecular (cancellous, or "spongy") bone. The structure and composition of individual bones varies, and is generally related to the specific function performed by the particular bone. Generally, an anatomical bone consists of about 25% by volume of specific bone tissue and about 75% by volume of bone marrow. Bone marrow consists of yellow and red bone marrow. Yellow bone marrow includes primarily fat cells (about 85% by volume), water (about 15% by volume) and a small fraction of protein (typically less than about 1% by volume). Red bone marrow mainly includes erythropoetic tissue elements, and its composition is approximately 40% water by volume, 40% fat by volume, and 20% protein by volume. The overall mass of red marrow typically decreases with age. This lost red marrow mass is replaced with yellow marrow. At any age, the proportion of red and yellow marrow is different for different anatomical bones. Of the specific bone tissue weight in any particular bone, only about 20% is organic matter (mainly collagen), about 70% is mineralized phase (crystals of hydroxyapatite and amorphous calcium phosphate) and about 10% is water.

In the foregoing discussion and in the description of the invention to follow, these definitions will be used. An "anatomical bone" is a structural, functional part of the skeleton such as the tibia, the radius, the calcaneus, for example. The term "bone" in general refers to a part of any of the previously mentioned anatomical bones, including cross-sections of any anatomical bone. "Bone tissue" is the tissue composition of the cortical bone and trabecular bone making up any anatomical bone. "Specific bone tissue" represents the part of bone tissue excluding any microscopic cavities, blood vessels and the like. The microscopic cavities include osteocytes, lacunae, canliculae, Haversian canals, and Volkmann's canals. "Bone matrix" is the specific bone tissue excluding any chemically bound water. The bound water is also known in the literature as the hydration shell. Bone matrix consists of organic matter, 95 percent of which is in the form of collagen fibers, and inorganic matter referred to as bone mineral. the foregoing definitions have been provided to clarity of the description to follow, because reconciliation of the various terminologies for bones and their components has been difficult since no techniques have been developed to measure the bone matrix quantity in vivo.

Bone continuously undergoes remodeling or turnover during a person's life. Older bone tissue is replaced at anatomically discrete sites with newly formed bone tissue to avoid cumulative skeletal fatigue damage. Approximately 20% of bone tissue is replaced annually by this process on a cyclical basis throughout the skeleton. There are five phases to bone remodeling: activation, resorption, reversal, formation and quiescence. The entire remodeling process occurs over approximately 4 to 8 months, with a range of 3 months to 2 years depending on the particular bone.

In bone growth, and during the remodeling process in a normal, healthy person, the organic matter remains a relatively constant fraction of the total specific bone tissue volume, while mineralization of bone occurs by replacement of water by the previously described mineral phase (crystals of bone mineral). Mineralization and crystal growth continue until there is no space left for further mineral expansion. Crystals form and grow within a fixed volume by displacement of water. The space between the crystals become smaller and smaller as the crystals grow, until eventually a state of maximum mineralization is achieved. For bone crystals to grow, mineral ions must diffuse in from fluid circulation. As the intercrystalline spaces become so small as to approach atomic dimensions, ions can no longer diffuse at appreciable rates. Specifically, polyvalent ions of calcium, which form a large part of bone mineral, are large and have high electric charge that prevents them, by electric repulsion, from entering narrow intercrystalline spaces. The same size spaces, however are accessible to univalent ions. Additional chemical evidence suggests that the water in calcified tissues is largely in chemically bound form.

b. Osteoporosis

Osteoporosis is a systematic skeletal disease characterized generally by low bone mass and microarchitectural deterioration of bone tissue, with a consequent increase in susceptibility to fracture. More specifically, in osteoporosis, the total volume of the anatomical bones remains unchanged during progress of the disease, but the bones show cortical thinning and development of porosis. Osteoporotic bones exhibit a specific bone tissue fraction and a bone mineral fraction of their total volumes which are less than their normal proportions of the particular anatomical bone's total volume. However, within the specific bone tissue, the proportions of mineral and organic matter remain relatively unchanged. The structural and chemical composition of the specific bone tissue in osteoporotic bone tissue is thus relatively indistinguishable from that of normal bone. This has made analysis of osteoporotic bone difficult using methods known in the art for analyzing bone.

c. Radiologic Bone Densitometry

The National Osteoporosis Foundation has issued specific and aggressive recommendations for managing and preventing osteoporosis in, *First guidelines for osteoporosis issues by National Osteoporosis Foundation in collaboration with multidisciplinary physician organizations* (news release Nov. 5, 1998). These guidelines include the use of BMD as the single most reliable tool for assessing bone strength and osteoporosis risk. The rationale for using BMD as a monitoring and predictive tool is that there is a well-established relationship between BMD and the ability of bone to withstand compressive, torsional and bending forces. A strong correlation between BMD and the load necessary to induce skeletal failure has been shown, for example, by Johnston and Melton, *Bone densitometry measurement and the management of osteoporosis*, Primer on Metabolic Bone Diseases and Disorders of Mineral Metabolism, American Society for Bone and Mineral Research, Society Office, pp. 93-100 (1996). In-vivo radiologic bone densitometry methods for diagnosis and therapeutic follow-up include:

I. Conventional skeletal radiography This method is relatively insensitive and bone loss is apparent only when bone mass has decreased by about 30–50%.

II. Radiographic photodensitometry. This method uses exposure to X-rays of a reference wedge alongside the area of interest in measuring the optical density of X-ray films of the bones in the area of interest.

III. Radiogrammetry. This method relies on an expected linearity of measurements of X-ray films made of cortical bone taken under standardized conditions. The radiogrammetry technique gives values for the cortical width of bone, from which the cortical area of the bone can be derived. This technique is accurate in predicting bone ash weight, but is less sensitive and less specific than absorptiometric measurements, because it does not account for trabecular bone density or cortical bone porosity.

IV. Single Photon Absorptiometry (SPA). This technique includes measurements related to attenuation by bone and soft tissue of a well-collimated gamma-ray beam. To account for soft tissue absorption, the body part being examined is immersed in a water bath that simulates a uniform soft tissue thickness. Single energy X-ray absorptiometry (SXA) is a related and newly developed technique suitable for scanning appendicular sites. It avoids the need for using specific radioisotopes.

V. Dual-energy Photon Absorptiometry (DPA). This technique has to be used, for example, to analyze proximal femur and vertebral bodies, which are very irregular bones. The irregularity make delineation of the bones difficult. Furthermore, these bones are surrounded by a widely varying amount of fat, muscle mass and, in the case of the spine, gastrointestinal organs which may be partially filled with gas. These factors limit the use of SPA and SXA. The different thickness of soft tissue can be accommodated by simultaneous measurement of the transmission of gamma ray of two different energies.

VI. Dual-energy X-ray Absorptiometry (DXA). DXA has now largely replaced DPA because of its greater precision, ease of use and freedom from several technical artifacts. There is no evidence to suggest that DXA has any disadvantages compared with DPA. The theory underlying DPA and DXA requires that there are only two energy absorptive components present, bone and soft tissue, each having uniform composition. In practice, fat has an additional component with attenuation characteristics that differ from those water, muscle and most organs. Fat is distributed non-uniformly in the region of the lumbar spine and may cause errors of up to 10% in estimation of spinal bone mineral mass. Errors can also be introduced by the presence of fat within the vertebral bone marrow.

VII. Quantitative Computed Tomography (QCT). Under appropriate conditions QCT may provide a measure of volumetric bone mineral density, and cancellous bone can be measured independently of the surrounding cortical bone. The biggest source of error in single X-ray QCT systems is the fat within the bone marrow. Accuracy errors of up to 30% may be introduced from the presence of fat in marrow. The accuracy of QCT may be improved by performing scans at two different X-ray energy levels. Errors of in vivo measurement are much higher than those made in vitro, but the precision of dual-energy QCT can be as high as 10%, much higher than the 2% obtainable with single-energy QCT. A wide range of radiation doses has been used to perform QCT, with values as high as 40 mGy for dual-energy measurement. This comparatively high radiation dose limits the number of repeated measurements that can be done to a single patient, for example, to monitor progression of osteoporosis.

VIII. Photon-scattering methods and neutron activation analysis. These techniques have been conceptually and experimentally developed for bone mineral density measurement. However, these techniques were not adequately assessed for screening.

IX. Ultrasound. Evaluation of bone by ultrasound is based on measurement of velocity, attenuation or reflection of ultrasonic energy imparted to the bone. Interest in these techniques is based on the fact that ultrasonic energy does not introduce ionizing radiation to the body, and may provide some information concerning the structural organization of the bone in addition to information concerning bone mass or density. Ultrasound attenuation measurement has not yet been proven for use as a screening tool. Ultrasound reflection measurement may provide some indication of the material properties of bone but has not been widely studied. Speed of sound has been shown to be a function of both the mass and the modulus of elasticity of the bone, but there have been no studies as yet examining whether or not the speed of sound provides a measure of bone "quality" and a better assessment of bone fragility than bone densitometry alone.

d. Magnetic Resonance Imaging, Particularly of Human Bone

Magnetic Resonance Imaging (MRI) instruments can be used for determining structural properties of a bone. Methods of using MRI measurements for determining the microstructure of a mass of trabecular bone are described, for example, in *A Review of Recent Advances in Magnetic Resonance Imaging in the Assessment of Osteoporosis*, S. Majumdar. and H. K Genent, Osteoporosis International, Vol. 5, No. 2, pp. 79–92 (1995).

Nuclear Magnetic Resonance (NMR) methods in general are among the most useful nondestructive techniques of material analysis. Particularly, non-invasive examination of a human body by means of NMR is extensive. Specifically, MRI and Magnetic Resonance Spectroscopy (MRS) have many useful application in medical diagnostics. Although Quantitative Magnetic Resonance (QMR) has fewer applications when compared with MRI and MRS, QMR is increasingly being used as a diagnostic tool. In general, NMR/MRI instruments known in the art for analyzing bone typically make measurements corresponding to an amount of time for hydrogen nuclei present in the anatomical bone to substantially realign their spin axes, and consequently their bulk magnetization, with an applied static magnetic field, as well as measurements related to the hydrogen density from within each image pixel. A superconducting electromagnet, conventional electromagnet or a permanent magnet typically provides the applied static magnetic field. The spin axes of hydrogen nuclei in the bone, in the aggregate, align with the static magnetic field applied by the magnet. Various sequences (selectable length and duration) of radio frequency (RF) magnetic fields are imparted to the bone to momentarily re-orient the nuclear magnetic spins of the hydrogen nuclei. RF signals are generated by the hydrogen nuclei as they spin about their axes due to precession of the spin axes. The amplitude, duration and spatial distribution of these RF signals are related to properties of the material which are being investigated by the particular NMR techniques being used.

In the field of in-vivo analysis of bone there have been numerous attempts to use all of the above mentioned Magnetic Resonance methods and techniques. Briefly, these techniques and their limitations are as follows:

I. MRS (magnetic resonance spectroscopy). U.S. Pat. No. 4,635,643 issued to Brown discloses an MRS method to quantify mineral content of a bone by recording a $^{31}$P spectrum in vivo and comparing it to a MRS spectrum of a reference standard having known concentration of reference minerals. A drawback to this technique is the fact that many human tissue types contain a variety of phosphates which yield $^{31}$P peaks within a very narrow chemical shift range. Thus resolving an individual peak within a $^{31}$P MRS spectrum of measurements made on a bone is very difficult. In addition, MRS requires very high homogeneity and strength of the static magnetic field, due to the required high spectral resolution of chemical shifts, making MRS equipment extremely expensive.

II. MRI (magnetic resonance imaging). U.S. Pat. No. 5,247,934 issued to Wehrli et al. discloses an MRI method for osteoporosis diagnosis. The essence of the method in the '934 patent is to make an image of the microstructure of trabecular bone, and based on this image and certain empirical criteria, to calculate several trabecular bone parameters such as trabecular thickness, intercept length and fabric tensor. Then, by comparing the obtained set of parameters with data corresponding to a trabecular bone having a known condition, the condition of the bone being examined is then determined. Disadvantages of the method in the '934 patent are first, the typical MRI in-vivo images provide pixel sizes of about 0.5 to 1 millimeters (mm) and section thicknesses of about 2 to 3 mm. This resolution is insufficient to analyze trabecular bone microstructures, which would require image resolution less than the average trabecular thickness, which is about 100 micrometers ($\mu$m). Images with a pixel size of 100×100×1000 micrometers, as described in the '934 patent, are about the smallest in-vivo pixel sizes which can be attained using the best currently available equipment. This resolution is still not sufficient to resolve trabecular bone microstructures. In addition there are fundamental limitations in MRI physics and technology as explained by Kuhn in, *NMR Microscopy—Fundamentals, Limits and Possible Applications*, ANGEWANDTE CHEMIE, International Edition in English, Vol. 29, No. 1, Jan. 1990, pp. 1–19. The fundamental limitations may limit future improvements in spatial resolution of MRI measurement. Technological limitations include requirements for higher signal-to-noise ratio, more homogeneous and stable static magnetic field, and stronger and more linear magnetic field gradients. Physical limitations include the spectral signal line width and the effect of chemical shift on the measurement.

III. QMR (quantitative magnetic resonance). U.S. Pat. No. 5,270,651 issued to Wehrli discloses the use of the QMR method. This relaxometry-type method avoids the necessity for complicated and expensive equipment, but fails to overcome several limitations, such as trabecular bone being the only bone analyzed. As in the MRI method, fluids that occupy the intratrabecular spaces are not a simple type fluid, but include a mixture of blood, lipids, proteins and other fluids each having an individual NMR relaxation rate. Therefore, the NMR relaxation time spectrum may be extremely complicated, the relaxation time spectrum is also patient and skeletal site dependent, and the correlation between the relaxation time spectrum and the physical condition of bone, such as reduced BMD and consequent increase in risk of fractures (and more specifically osteoporotic conditions) is questionable. Internal magnetic field gradient distribution, which is the underlying phenomenon of this relaxometry QMR method, is not only a function of trabecular bone microstructure but also depends on the spatial distribution of the magnetic susceptibility of the materials being analyzed by NMR techniques. The assumption that the magnetic susceptibility of bone tissue and bone marrow is constant, as is required for this technique, is not highly accurate.

e. NMR techniques for analyzing materials other than human bone have been developed. These techniques, which are relevant to bone analysis, include the following:

NMR methods for quantitative analysis of moisture level or "solid" to "liquid" ratio are known in the art. Measuring fat content in margarine has become a very important application of such techniques. A more general approach is described, for example, in U.S. Pat. No. 5,539,309 issued to Van Wyk et al. which discloses a concept of "solid" to "liquid" ratio determination. Generally the technique works where there exist physically distinct phases having relaxation times which may be characterized as "fast " and "slow" relative to one another. This method is quite effective in cases when the relaxation times of the two phases are very different. The technique disclosed in the Van Wyk et al '309 patent, however, has low accuracy where the relaxation times are only marginally different, or when used for mixtures including several phases, such as for example, determining bound water content of fluid-bearing porous earth formations. Examples of similar applications includes: U.S. Pat. No. 5,818,228 issued to Menon et al. which discloses using a similar technique for measurement of the resin content of a composite material by NMR. U.S. Pat. No. 4,701,705 issued to Rollwitz which discloses a method for determining moisture of a material by determining the total hydrogen density of the material.

f. NMR technical issues relevant to NMR bone analysis include the following:

NMR techniques in general, including all the aforementioned techniques, could be more effective if their signal-to-noise ratio could be improved significantly. This would lead to better precision, accuracy and spatial resolution irrespective of the selected NMR technique. This fact is recognized in an apparatus for noninvasive, localized, in-vivo examination of tissue, including bone, which is disclosed in U.S. Pat. No. 4,442,404 issued to Bergmann. The essence of the method and apparatus described in the Bergmann '404 patent is to use a detection coil maintained at superconducting temperature to achieve a high signal-to-noise ratio. This technique has not been used on a commercial basis due to engineering difficulties, and in many cases thermal noise is generated not only in the detection coil but also in the sample itself because the sample is electrically conductive.

Despite extensive research and development into methods of characterizing bone and the cause and treatment of osteoporosis, there is still a need for reliable, accurate, precise and specific non-invasive methods for acquiring information relating to the bone and for detecting, diagnosing and monitoring diseases such as osteoporosis.

SUMMARY OF THE INVENTION

One aspect of the invention is a method for analyzing a bone using nuclear magnetic resonance (NMR) measurements. The method includes measuring a nuclear magnetic resonance signal which corresponds to an amount of hydrogen within a selected, known, discrete volume of the bone. The selected volume is large enough so that the bulk properties of the bone within the selected, known, discrete volume correspond to the NMR signal. A bone matrix volume is then determined from the NMR signal. In one embodiment of the invention, the measured NMR signal is a steady state free precession amplitude. In one embodiment of the invention, the spatial position of the selected known discrete volume is determined by a sensitive point technique. One example of a sensitive point technique includes imparting a substantially homogeneous static magnetic field to the bone and superimposing mutually orthogonal oscillating gradient magnetic fields onto the static magnetic field. The static magnetic field has substantially constant amplitude only within the selected discrete volume. In another example of this embodiment, a bone mineral density which corresponds to the bone mineral density determined by X-ray absorptiometry is determined from the bone matrix volume. In another example, the bone matrix density is determined directly from the NMR signal thus measured.

Another aspect of the invention is a method for evaluating a bone for its condition. The method of this aspect of the invention includes measuring an NMR signal from within a selected, known, discrete volume of the bone. The known volume is large enough so that the NMR signal corresponds to the bulk properties within the known discrete volume. The NMR signal is localized within a part of an anatomical bone having bulk properties indicative of the condition of the bone, for example, within trabecular bone within the spine, femur, radius or calcaneus. Localization is performed in one example by moving the selected known discrete volume until an amplitude of the signal reaches a value corresponding to the trabecular bone. The signal thus localized reflects the bone matrix volume disposed in the discrete selected volume. In one embodiment of the invention, the measurement is repeated at selected times to detect changes in bone matrix volume which correspond to the condition of the bone.

Another aspect of the invention is an apparatus for measuring NMR properties of the calcaneus bone. The apparatus includes a receptacle adapted to receive the foot. The foot contains the calcaneus bone therein. The receptacle is adapted to substantially immobilize the foot. The apparatus includes a magnet for inducing a static magnetic field within the calcaneus bone, a radio frequency pulse generator and an antenna coupled thereto positioned to induce a radio frequency magnetic field in the calcaneus bone to excite nuclear magnetic resonance therein, a receiver and a transceiver antenna coupled thereto to detect NMR signals originating in the calcaneus bone, and means for localizing generation and detection of the NMR signals from within a selected known volume within the calcaneus bone. The apparatus includes means for calculating a property of specific bone tissue within the calcaneus bone. In one example of the apparatus, the radio frequency pulse generator and the receiver are adapted to detect steady state free precession amplitude signals. In one example of the apparatus, the NMR correspond to a number of hydrogen nuclei within a selected known volume in the calcaneus bone. The means for calculating is adapted to determine a bone matrix volume within the selected known volume. In one example, the means for localizing includes gradient coils disposed about the foot. The gradient coils are coupled to a source of alternating current so that the static magnetic field induced in the calcaneus bone is substantially invariant in amplitude only within the selected known volume. In another example, the magnet and transceiver antenna are structured so that the discrete known volume is disposed entirely within the calcaneus bone.

DETAILED DESCRIPTION

Figure 1:
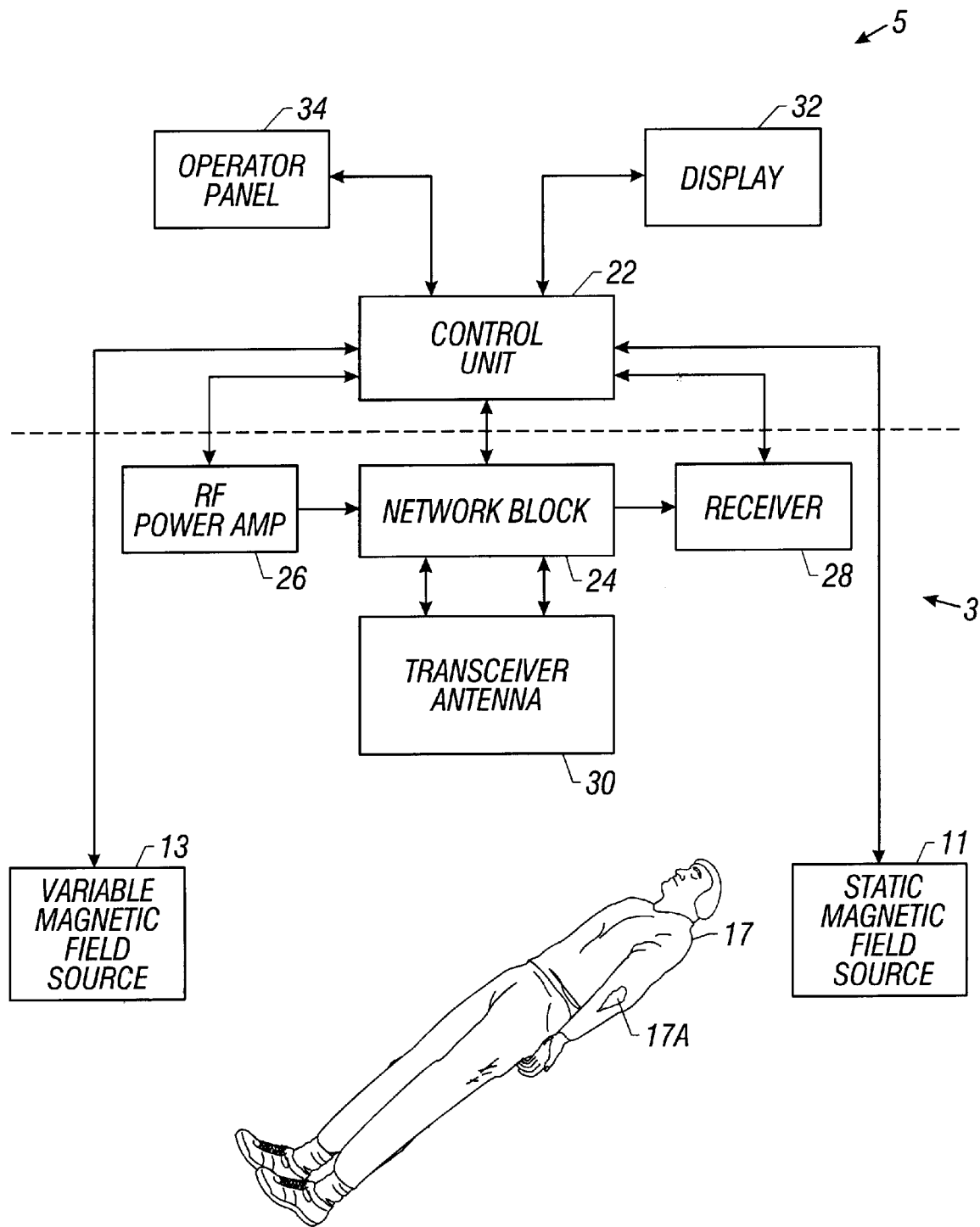
FIG. 1 is a simplified diagram illustrating a nuclear magnetic resonance system for bone analysis.

FIG. 1 shows in general form one example of a nuclear magnetic resonance (NMR) system for bone analysis. The NMR system includes a first portion 3, which is arranged to be located near a part of a patient's body 17 which includes a bone 17A to be examined by the NMR system. The first portion 3 includes a static magnetic field source 11 which induces a static magnetic field in the bone 17A. The static field source 11 may include one or more permanent magnets, conventional electromagnets or superconducting electromagnets. The first portion 3 of the NMR system also includes a variable magnetic field source 13, which may comprise one or more gradient coils (not shown in FIG. 1) to induce variable gradient magnetic fields in the bone 17A. The term "static" as applied to the magnetic fields in this description means that the amplitude of the field is not variable in time or direction, nor does the spatial distribution of the field vary in time during the NMR measuring cycle. The field amplitude, however, is not necessarily homogeneous in its spatial distribution. The term "variable" as used to describe magnetic fields herein means that the field amplitude is variable in space, direction and/or in time during an NMR measuring cycle, but the variation occurs at rates which are much slower than radio frequencies ("RF") for which magnetic resonance condition are met for nuclei under investigation. Both the source of the static magnetic field 11, if electromagnetic, and the variable magnetic field source 13, can be powered and controlled by a control, processing, monitoring and safety unit (control unit) 22, which in this example is included in a second portion 5 of the system.

The first portion 3 of the NMR system also includes an RF magnetic field transceiver antenna (antenna) 30. The antenna 30 can be interconnected to a network block 24. The network block 24 typically includes circuits, none shown separately in FIG. 1, such as a transceiver tuning circuit, which may include a series of resonance capacitors, a transmitter to receiver switch and both "to-transmitter" and "to-receiver" matching circuitry.

The network block 24 can be coupled both to an RF power amplifier 26 and to a receiver 28. While the network block 24, the RF power amplifier 26 and the receiver 28 are shown in FIG. 1 shown as being located inside the first part 3 of the NMR system, it is to be understood that the whole network block 24, the RF power amplifier 26 and the receiver 28, or any part of these elements may be disposed partially or entirely within the second part 5 of the NMR system. The particular locations of the network block 24, the RF power amplifier 26 and the receiver 28 or any parts thereof are not to be construed as a limitation on the invention. The network block 24 in this example is controlled by the control, processing, monitoring and safety unit 22, which in this example also controls the timing and operation of, and provides power to, the RF power amplifier 26 and provides the receiver 28 with a phase reference and other coordination signals. The RF power amplifier 26 provides a high power signal to drive the transceiver antenna 30 for generating an RF magnetic field in a sensitive volume in the bone 17A which is to be examined by the NMR system.

During reception of NMR signals from the bone being analyzed 17A, voltages are induced in the antenna 30, the output of which can be conducted via a preamplifier (not shown separately) to the receiver 28, and then to the control, processing, monitoring and safety unit 22. Usually the preamplifier forms part of the receiver 28, but may preferably be positioned as closely as possible to the antenna 30 due to signal processing requirements, and therefore can be considered to be part of the antenna 30 for purposes of this description.

The control unit 22, which can be operated through a remote operator panel 34 can include a computer (not shown separately) for processing the received signals, and can transfer the processed signals, and results of analysis thereof, to a display 32 for presentation in any form which is useful to those skilled in the art of NMR measurements of bone properties.

Figure 2:
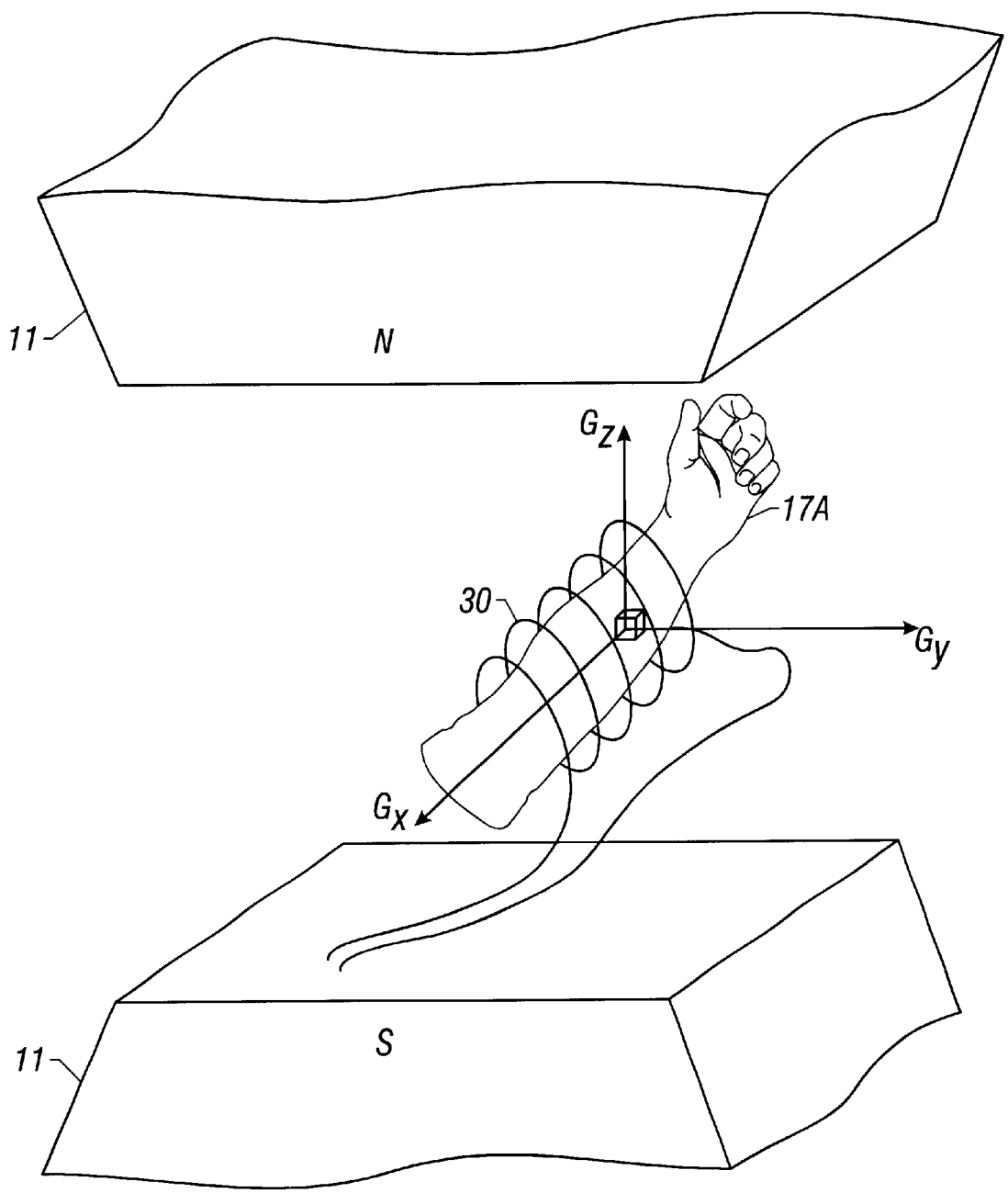
FIG. 2 shows a human arm disposed in one example of an NMR measuring apparatus to perform one example of the technique of the invention

FIG. 2 shows one embodiment of the transceiver antenna 30 and the static magnetic field source 11 in more detail. In this example, the static field source 11 can be a permanent magnet arranged to induce a static magnetic field polarized normal to the longitudinal axis of the bone 17A (referred to herein as the x axis). The direction of polarization of the static magnetic field in this example is defined as being along the z axis. In this example, the analyzed bone 17A is the radius in the forearm, but as previously explained, the particular anatomical bone which is analyzed is not critical to the invention. The transceiver antenna 30 in this example is a coil wound so that its axis, and consequently the magnetic field which it induces within the bone 17A, are substantially perpendicular to the static magnetic field induced in the bone 17A by the magnet (static field source 11). The antenna 30 may have any other convenient configuration which results in an RF magnetic field being induced in the bone 17A perpendicular to the static magnetic field.

Gradients of the z axis component of the magnetic field in this example are also induced in the bone 17A along mutually orthogonal axes, preferably x,y, and z axes as shown in FIG. 2 as $G_X$, $G_Y$ and $G_Z$. The purpose of the gradient magnetic fields is to localize the selected, known volume from which the NMR signal is detected in the transceiver antenna 30.

Figure 3:
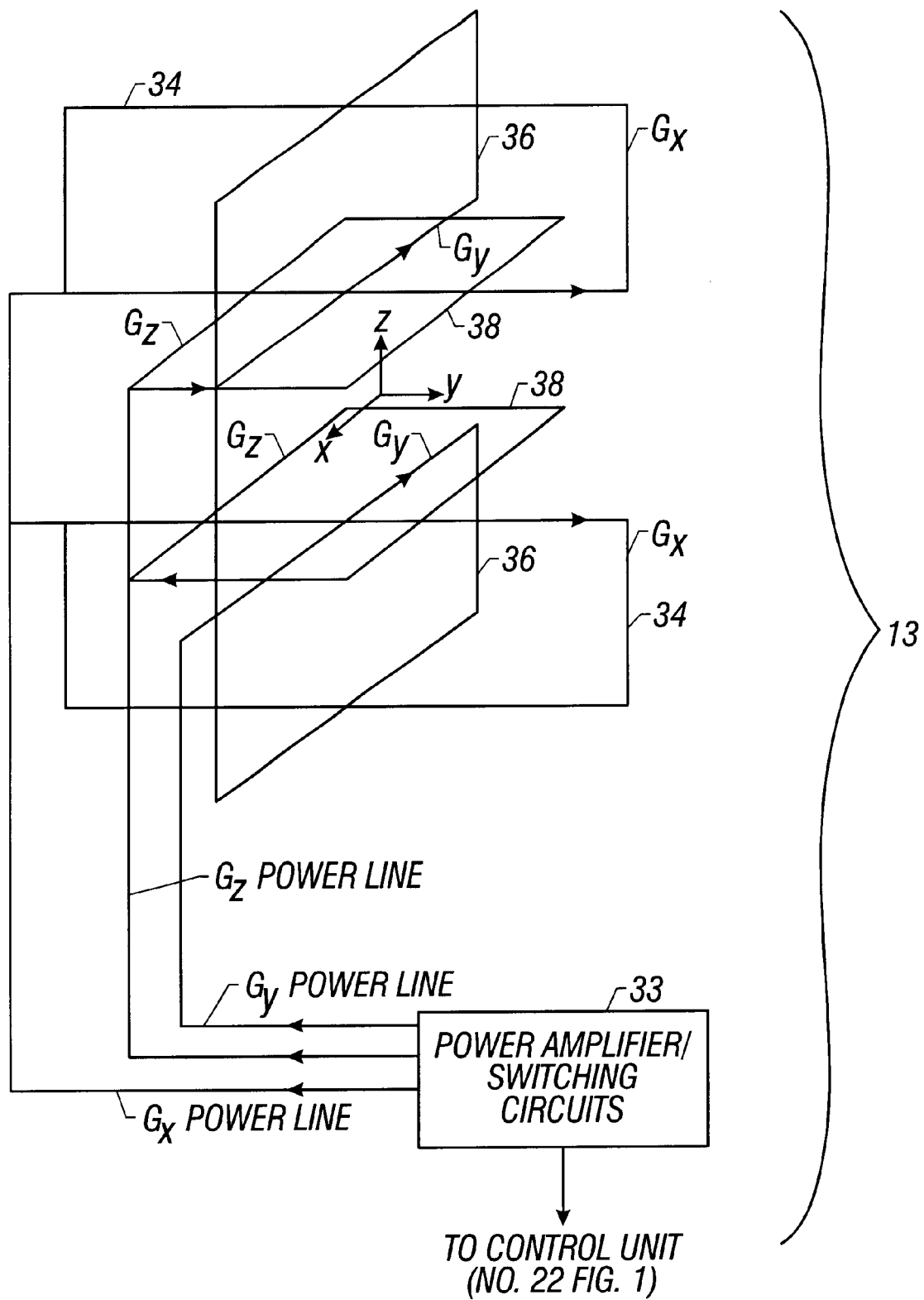
FIG. 3 shows an arrangement of gradient magnetic field coils which can be used in one example of a measuring apparatus to perform one example of the technique of the invention.

FIG. 3 shows in simplified form an example of gradient field coils which can be used to localize the NMR signal for purposes of the invention. The $G_X$ gradient is developed by passing current from a power amplifier/switching circuit 33 along $G_X$ power line to gradient coils 34. Similar connections can be made for $G_Y$ gradient coils 36 and for $G_Z$ gradient coils 38. The gradient coils 34, 36, 38 are arranged substantially orthogonally. In addition, the current passing through the gradient coils 34, 36, 38 in this example is low frequency AC having particular magnitude and frequency, so that only a selected, small, discrete volume in space between the gradient coils 34, 36, 38 has a substantially invariant amplitude magnetic field therein. This discrete volume is the source of substantially all the NMR signal detected by the transceiver antenna (30 in FIG. 2). Localization of the NMR signal by applying alternating gradients to a static magnetic field is known in the art and is described, for example, in P. Mansfield and P. G. Morris, *NMR Imaging in Biomedicine*, p. 98, Academic Press, New York, 1982. The particular position in space of the discrete volume can be selected, for example, by applying appropriate amplitude bias gradients to the AC gradients, such as by applying unbalanced current in a pair of coils through separate, independent power supply outputs. Other methods for selecting the spatial position of the discrete volume are also known in the art and are explained in the Mansfield and Morris reference, above, for example.

An important aspect of the selected discrete volume is that it should be large enough so that the NMR hydrogen (proton) signal measured from the selected, discrete volume is related to the bulk NMR properties extant within the selected discrete volume. According to results published by Hildebrand et al. in *Direct Three-Dimensional Morphometric Analysis of Human Cancellous Bone: Microstructural Data from Spine, Femur, Iliac Crest, and Calcaneus*, Journal of Bone and Mineral Research, Vol. 14, No. 7, July 1999, pp. 1167–1174., trabecular thickness measured in the laboratory ranges from 82 micrometers ($\mu$m) to 284 $\mu$m and directly calculated trabecular separation ranges from 0.45 millimeters (mm) to 1.31 mm. Discrete volume sizes for trabecular bone which will work with the invention include those having linear dimension longer than approximately several trabecular separations. Discrete volumes used for measuring properties of cortical bone may be substantially smaller. Prior art NMR bone analysis techniques include developing an image of the microarchitecture of the trabecular bone being analyzed. Developing such an image necessitates selecting a sensitive volume (equivalent to the selected discrete volume) size for each image pixel which is smaller than the typical trabecular thickness, and measurements therefrom are therefore not representative of the bulk NMR properties within such sensitive volumes. An advantageous aspect of the invention is that the discrete volume should be large as compared to the discrete volume used in typical NMR imaging techniques. The relatively large discrete volume results in improved signal-to-noise of the measurements being made.

The NMR signal being measured in this example is related to the amplitude of voltages detected by the transceiver antenna (30 in FIG. 2). The NMR signal amplitude, in turn, is related to the number of protons (hydrogen nuclei) disposed within the selected discrete volume. One suitable technique for measuring NMR-induced voltages related to proton numbers from within the discrete volume is known in the art as the steady state free precession (SSFP) technique.

This technique includes passing a series of RF power pulses through the transceiver antenna (30 in FIG. 2) at the nuclear magnetic resonance frequency, where the pulses have a duration sufficient to reorient the magnetic spins of the protons by about 90 degrees from alignment with the static magnetic field imposed by the source (11 in FIG. 2). This technique, variations of the SSFP technique, and other measurement techniques are also described in the Mansfield and Morris reference, referred to above, for example.

Figure 4:
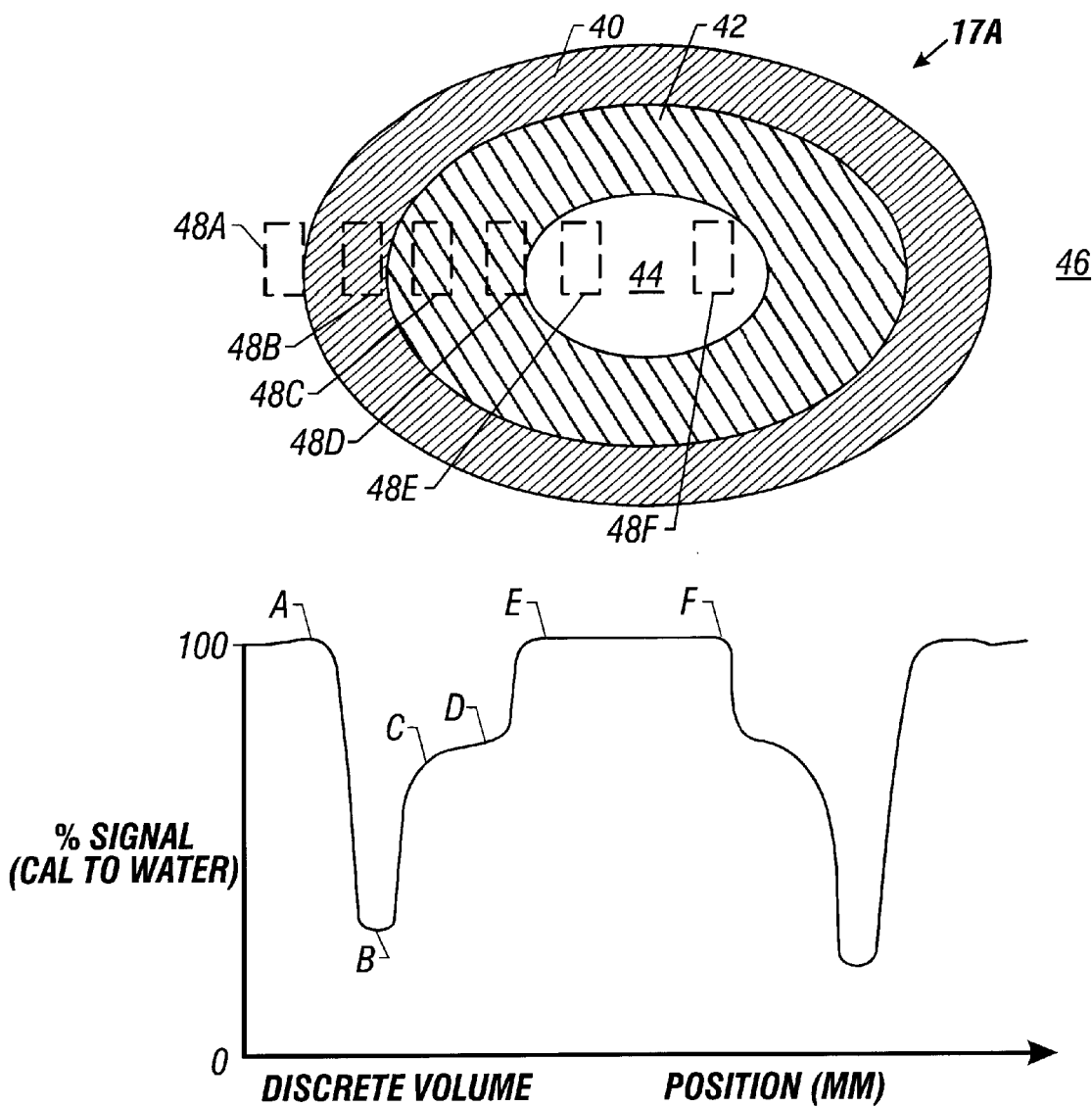
FIG. 4 shows a graph of expected NMR signal amplitude with respect to position of a discrete sensitive volume within bone and various tissues surrounding.

FIG. 4 shows, in simplified form, the expected response of the total proton measurement as it is made from within various discrete volumes across a cross-section the bone 17A being analyzed. The bone 17A includes a layer of densely mineralized cortical bone 40 on its exterior. The bone 17A also includes trabecular bone tissue 42 and marrow 44, the compositions of which have been described in the Background section herein. The soft tissues which surround the bone 17A are shown generally at 46. The selected discrete volume is shown at various locations at 48A through 48F. As the selected discrete volume is moved through the bone 17A (such as by changing the bias gradients as explained previously or by relative movement of bone with respect to the measurement apparatus), the total amplitude of the NMR signal, shown on the graph at the bottom of FIG. 4, will correspond to the type of tissue in which the discrete volume is positioned. For example, when the discrete volume is located within the soft tissue 46, such as shown at 48A, its amplitude will be substantially the same as the amplitude of the signal when measured in water (or other material having NMR response similar to water), this amplitude being shown in FIG. 4 at A. At 48B, the discrete volume is located substantially within the cortical bone 40, and the signal amplitude will drop, as shown at B, to a value corresponding to the much lower proton amount per unit volume of cortical bone 40. Within the trabecular bone 42, for example at 48C and 48D, the signal amplitude C, D, respectively, will have some intermediate value depending on the density of the trabeculae in the trabecular bone 42. At 48E and 48F, the discrete volume is positioned within the marrow 44 and has a signal substantially the same as the signal from within soft tissue, the marrow signal shown at E and F. The sizes of the cortical 40 and trabecular 42 bones and the marrow 44 are not to true scale and are only shown in FIG. 4 to illustrate in principle this particular example of localizing the NMR signal within a selected portion of the bone 17A. As will be further explained, the signal originating in the trabecular bone 42 is of particular interest in identifying certain bone diseases such as osteoporosis. Making measurements within the trabecular bone should not be considered as a limitation of this invention, however. It is clearly within the contemplation of this aspect of the invention that measurement made from within cortical bone or a combination of trabecular and cortical bone may be of interest in the study of particular bone conditions.

When the discrete volume, and consequently the NMR signal, are localized within bone tissue, the amplitude of the signal thus measured corresponds to the amount of hydrogen-bearing fluid from within the bone tissue. The bone matrix volume, as previously explained in the Background section herein, is the difference between the total volume occupied by the discrete volume and the fluid volume within the discrete volume. Therefore the method of this aspect of the invention provides a non-invasive technique whereby the bone matrix volume in a selected discrete volume of an anatomic bone can be determined in vivo, which was difficult to perform using prior art NMR/MRI techniques. Measurement of the bone matrix volume within a particular known volume of anatomical bone has diagnostic value to physicians in evaluating the condition of the bone tissue.

A particular embodiment of the invention which improves the accuracy of measurement of bone matrix volume includes measuring hydrogen (numbers of protons) signal using equipment and measurement techniques that have a system dead time of no more than about 200 microseconds. The system dead time can be minimized by techniques known in the art including using a relatively high amplitude static magnetic field, so that the NMR frequency is correspondingly high, keeping the size of the transceiver antenna (30 in FIG. 2) and gradient coils (34, 36, and 38 in FIG. 3) to a minimum. Keeping the size of the antenna 30 and coils 34, 36, 38 to a minimum is facilitated by building the NMR system to measure only selected body parts rather than the entire body. It has been determined that fully mineralized bone includes chemically bound water (hydrogen), small blood vessels and cavities which induce NMR signals having a very short decay time spectrum. The NMR signal from these substances has typically been ignored in NMR techniques used to image parts of the body, primarily because of the relatively long system dead time of typical NMR imaging equipment. As a result, the significance of the short decay time signal has previously gone unnoticed. It should be clearly understood that using equipment and techniques having short dead time to measure the rapid-decaying portion of the hydrogen signal is only provided to improve the accuracy of the technique of the invention. It is not necessary to measure the rapid-decaying signal in order to practice the invention. As previously explained, a measurement which has diagnostic value is the bone matrix volume. The bone matrix volume, which is the difference between the total volume of the anatomical bone and the fluid contained therein can be readily determined using NMR measurements which do not include so-called "fast" (short decay time) NMR signal components.

The measurement of bone matrix volume made as previously explained can be used for diagnostic purposes. It has been determined, however, that in bone tissue there is a strong correlation between the NMR hydrogen signal, which may include the short decay time signal, and the bone mineral density as measured by X-ray techniques. This correlation can be used to identify bone tissue which has a lower than normal bone mineral fraction of the bone volume, and consequent increased risk of stress-induced failure. This correlation was established by experiment on bovine tibia cut into standard size samples for analysis in both NMR equipment and in dual energy X-ray bone mineral densitometry equipment. The samples were about 1 inch (2.54 cm) diameter cylinders having lengths ranging from about ¼ inch (0.51 cm) to 2 inches (5.08 cm). The NMR relaxation spectra of the samples were measured using a MARAN NMR relaxometry instrument made by Resource Instruments, Ltd., Unit 13, Thorney Leys Business Park, Whitney, Oxfordshire, United Kingdom. The samples were also analyzed for bone mineral content using the dual energy X-ray absorptiometry technique (DXA) referred to in the Background section herein using a model QDR-2000 instrument made by Hologic Corp., 590 Lincoln St., Waltham, Mass. The samples were weighed on an electronic balance, and the volume of each sample was determined using a buoyancy technique.

Figure 5:
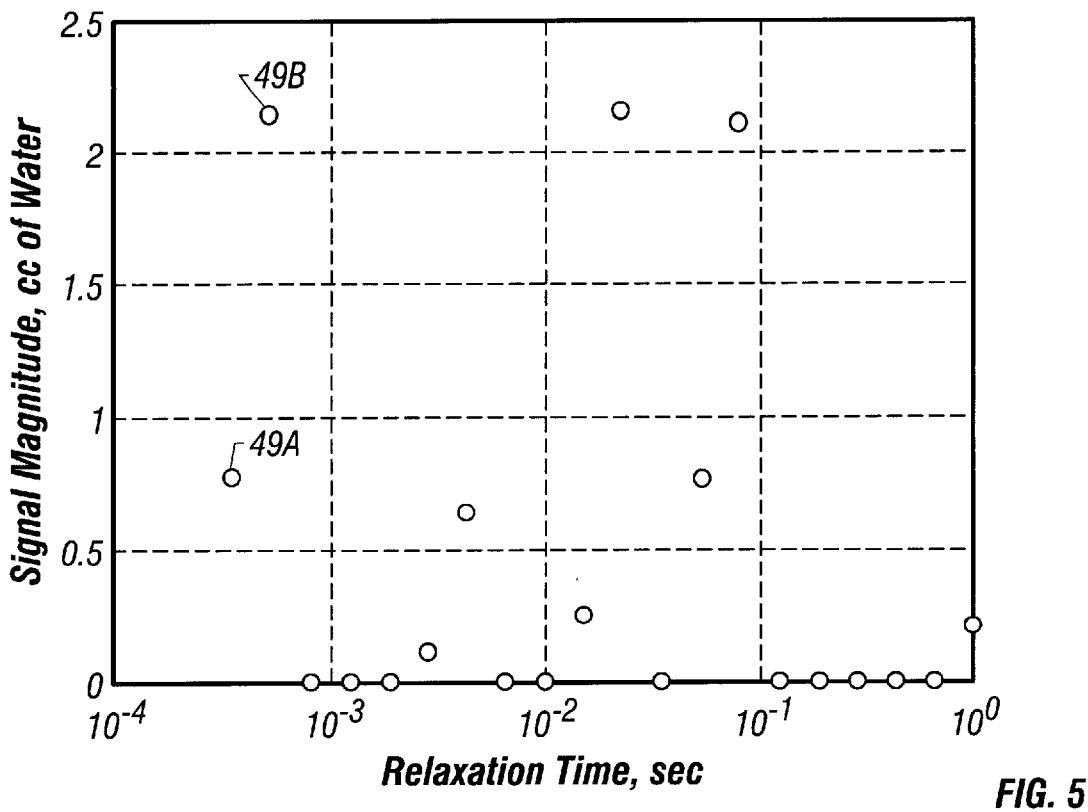
FIGS. 5 and 6 show a transverse ($T_2$) relaxation time spectrum of bone samples used to establish a correlation used in one embodiment of the invention.
Figure 6:
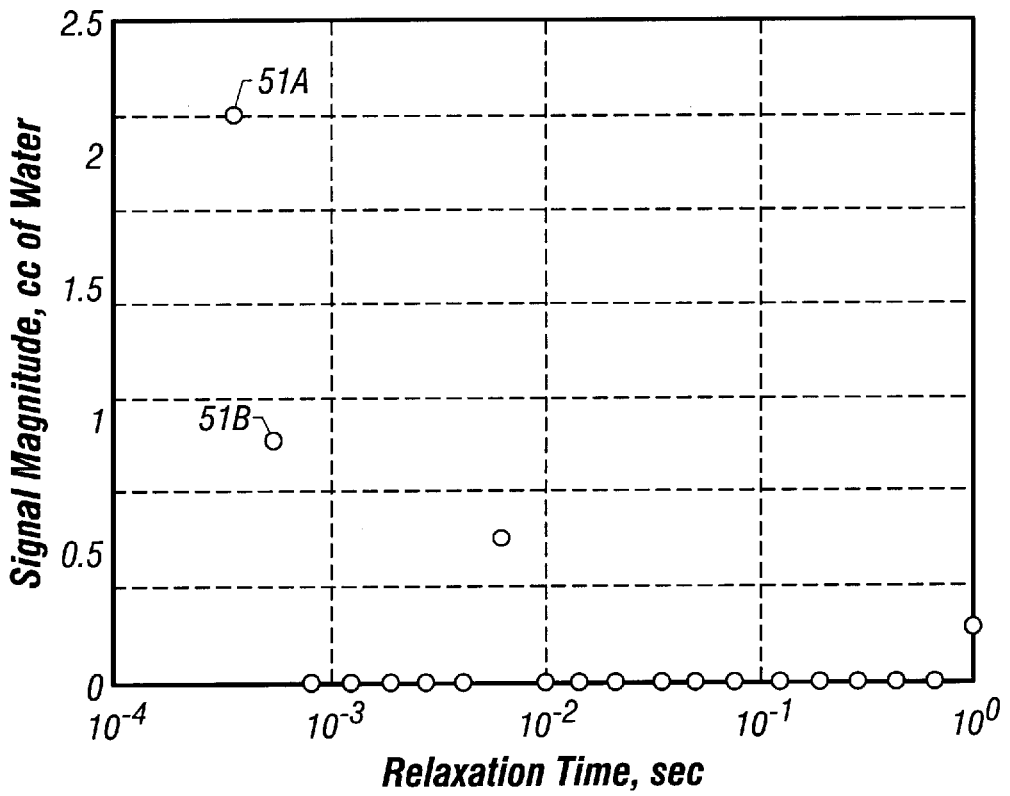

NMR relaxation spectra from the bovine tibia experiments are shown for different representative samples in FIG. 5 and FIG. 6. In FIG. 5, a relatively large amplitude, expressed in units of cubic centimeters (cc) of water in the sample volume, is present at points 49A and 49B for the relaxation time of about 0.7 milliseconds. This same large amplitude is observable at 51A 51B in FIG. 6. This large amplitude signal corresponds to the bound water in mineralized bone. Slower relaxation time components of the spectra correspond to blood, fat, water and other hydrogen-containing fluids present in the bone sample. The sum of all the amplitudes in each of FIGS. 5 and 6 corresponds to the equivalent volume of water in each sample.

Figure 7:
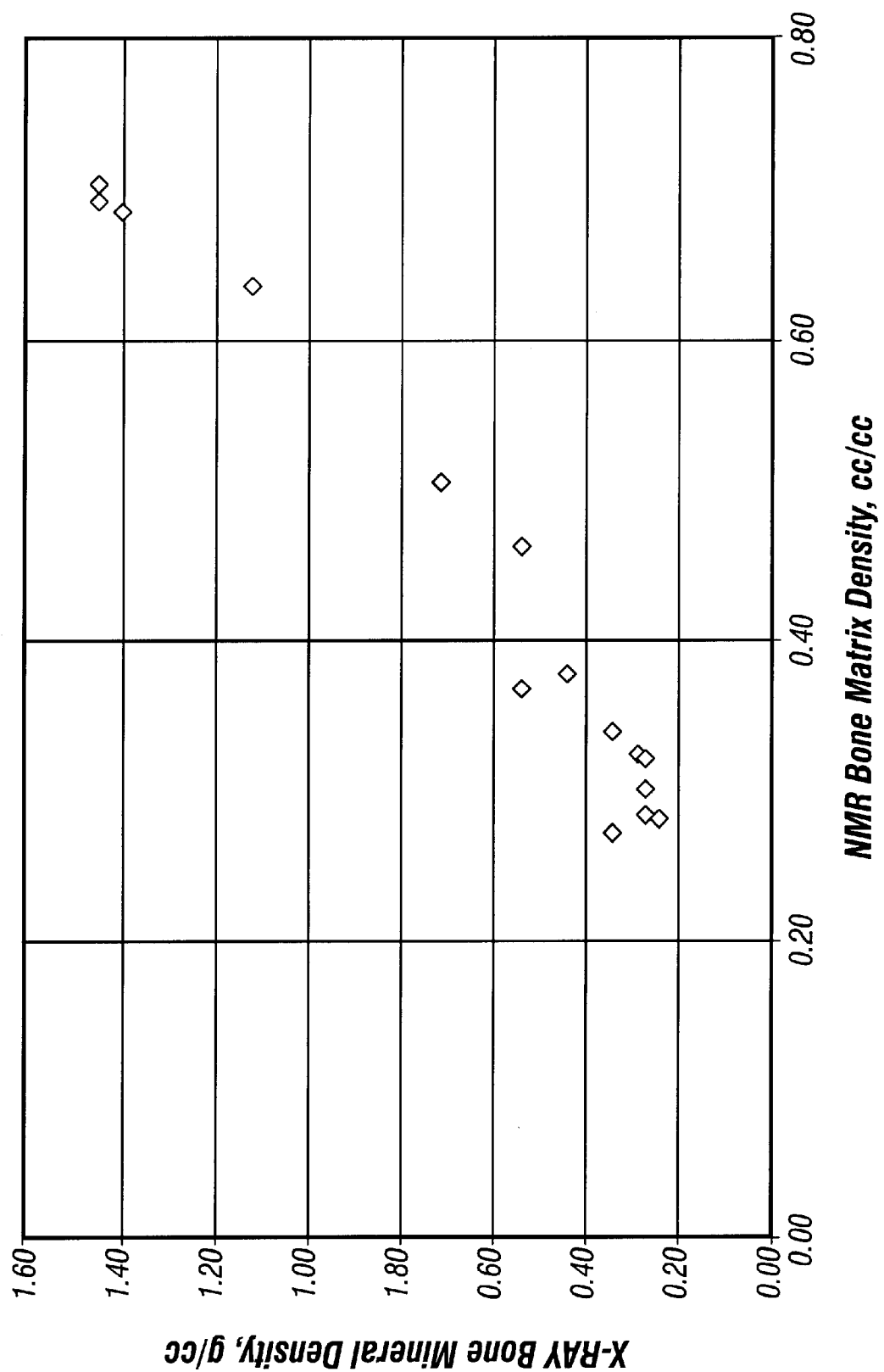
FIG. 7 shows a graph of the NMR-determined bone matrix density with respect to X-ray determined bone mineral density.

Having measured for each sample a total sample volume, the liquid volume in each sample having been determined from the NMR measurement, a corresponding bone matrix volume was calculated by subtracting the NMR-determined fluid volume in each sample from the total sample volume. The calculated bone matrix volume was then compared with bone mineral density determined by X-ray absorptiometry. A graph showing this comparison can be observed in FIG. 7. As shown in FIG. 7 there is a high degree of correspondence between the NMR-determined bone matrix volume and X-ray-determined bone mineral density. The correlation between bone matrix volume and bone mineral density for human bone can be similarly established by experiment on human bone, such as from cadavers. A correlation between the NMR hydrogen signal amplitude and the bone mineral density can thus be established for any particular type of bone under examination. The amplitude of the NMR hydrogen signal can then be used to directly determine a bone mineral density which is equivalent to the bone mineral density which would be determined by X-ray absorptiometry. The measurement of the numbers of hydrogen nuclei within the selected, known discrete volume can therefore be used as a diagnostic measurement in a manner similar to X-ray measurements of bone mineral density.

Figure 8:
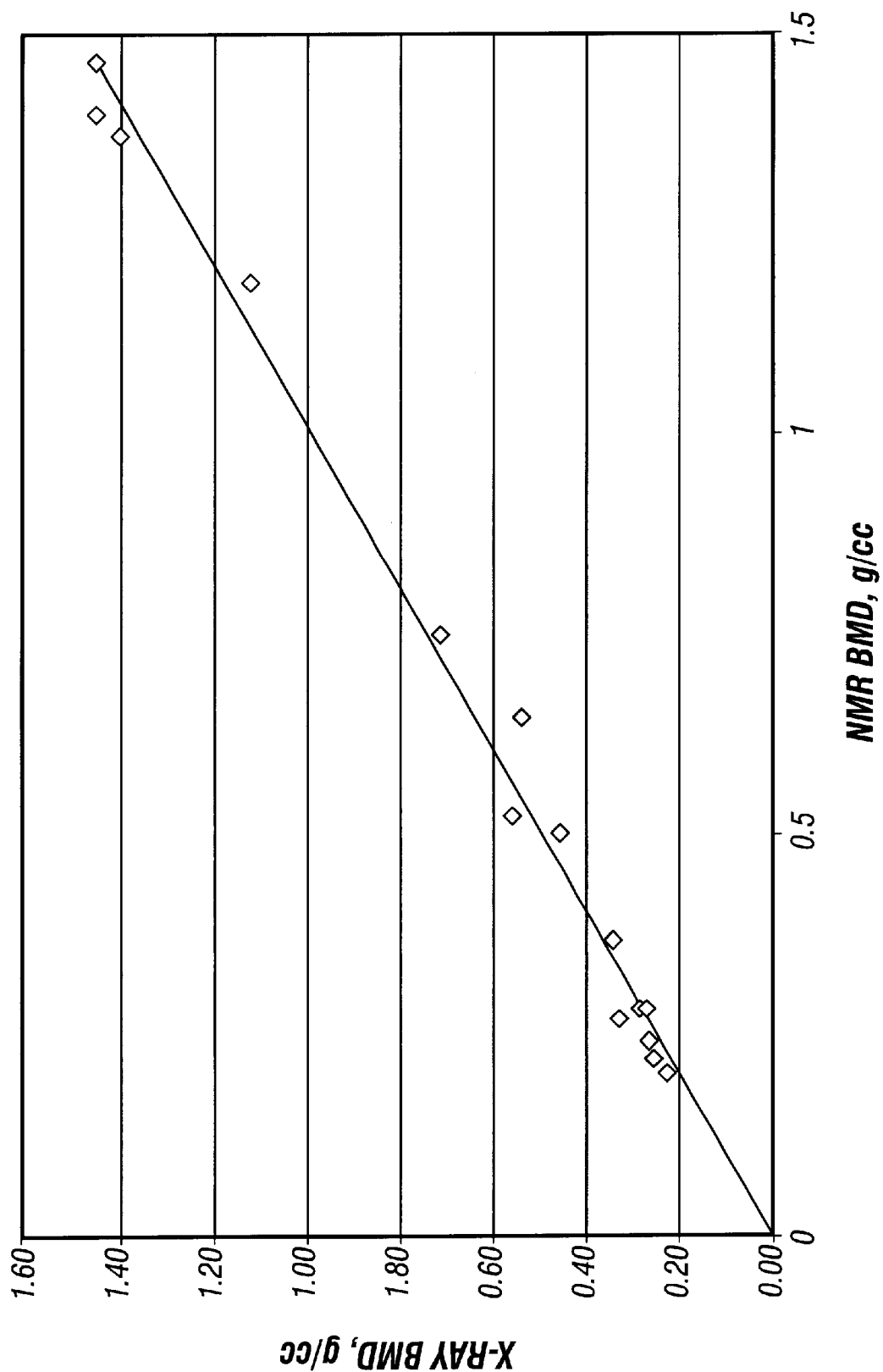
FIG. 8 shows a graph of the NMR-determined bone mineral density with respect to X-ray determined bone mineral density.

A graph in FIG. 8 shows, for the bovine tibia samples just described, correspondence between bone mineral density calculated using the NMR signal with bone mineral density determined using X-ray absorptiometry as previously described. Bone mineral density from NMR measurements is calculated by subtracting the liquid weight in each sample from the total weight of each sample (yielding a bone matrix weight), and dividing this amount by the total volume of each sample. The liquid weight is directly determinable from the liquid volume determined from the NMR signal assuming the specific gravity of the liquid is the same as that of water, about 1.0. In vitro techniques, such as described above, or in vivo techniques using X-ray absorptiometry can be used to calibrate any gain and offset in the correspondence between the NMR bone mineral density and the X-ray bone mineral density for any particular apparatus used to make NMR measurements according to the method of the invention.

The technique of the invention can be summarized as follows. An NMR signal is measured which corresponds to the amount of hydrogen within a selected known volume of anatomical bone. The NMR signal corresponds to the bone matrix volume of the anatomical bone under examination.

The spatial position of the selected known volume can be specifically selected by observing the NMR signal amplitude as an NM excitation volume is moved through the anatomical bone and the surrounding tissue. In one example, when the amplitude reaches a localized plateau at a value intermediate to that of mineralized bone and the soft tissue surrounding, the known volume is substantially in trabecular bone. The bone matrix volume can be used intermediately, or the hydrogen signal amplitude can be used directly, to determine a bone mineral density in the selected discrete volume.

Localization of the NMR total hydrogen signal from within trabecular bone provides a technique which can be used to evaluate bone for osteoporosis. In prior techniques NMR is used to construct an image of the trabecular bone, and the image is then integrated to determine the total fluid content of a known volume of anatomical bone, thereby to estimate bone density. Bone density in trabecular bone is believed to be strongly related to the strength of a particular anatomical bone and the ability of the anatomical bone to resist fracture. In prior art techniques, the NMR image is limited to the fluid part of the trabecular bone, primarily due to the relatively long dead time of the equipment used for patient imaging. Mineralized bone typically was considered "black" or devoid of any useful NMR signal. Accuracy of these techniques for determining any measure of bone density or mineral content is limited primarily because of the limits of resolution of the image in the fluid part of the bone. Due to these resolution limits, among other reasons, the total fluid volume was not calculated to a sufficiently high degree of accuracy. The method of the invention has the advantage of measuring the total amount of hydrogen in the selected volume, in a manner much less affected by the resolution limits of conventional imaging techniques. The high degree of correspondence between the bone matrix volume determined using the technique of the invention and bone mineral density measured by X-ray absorptiometry means that the technique of this invention can be applied to analysis of bone for osteoporosis or other disease identifiable by abnormal bone mineral density. For example, the method of the invention could include measuring the NMR hydrogen signal from a discrete volume within an anatomical bone section having a large amount of trabecular bone, such as the calcaneus. These measurements can be repeated at selected intervals over a period of time to detect changes in the volume of specific bone tissue in the trabecular bone.

Figure 9:
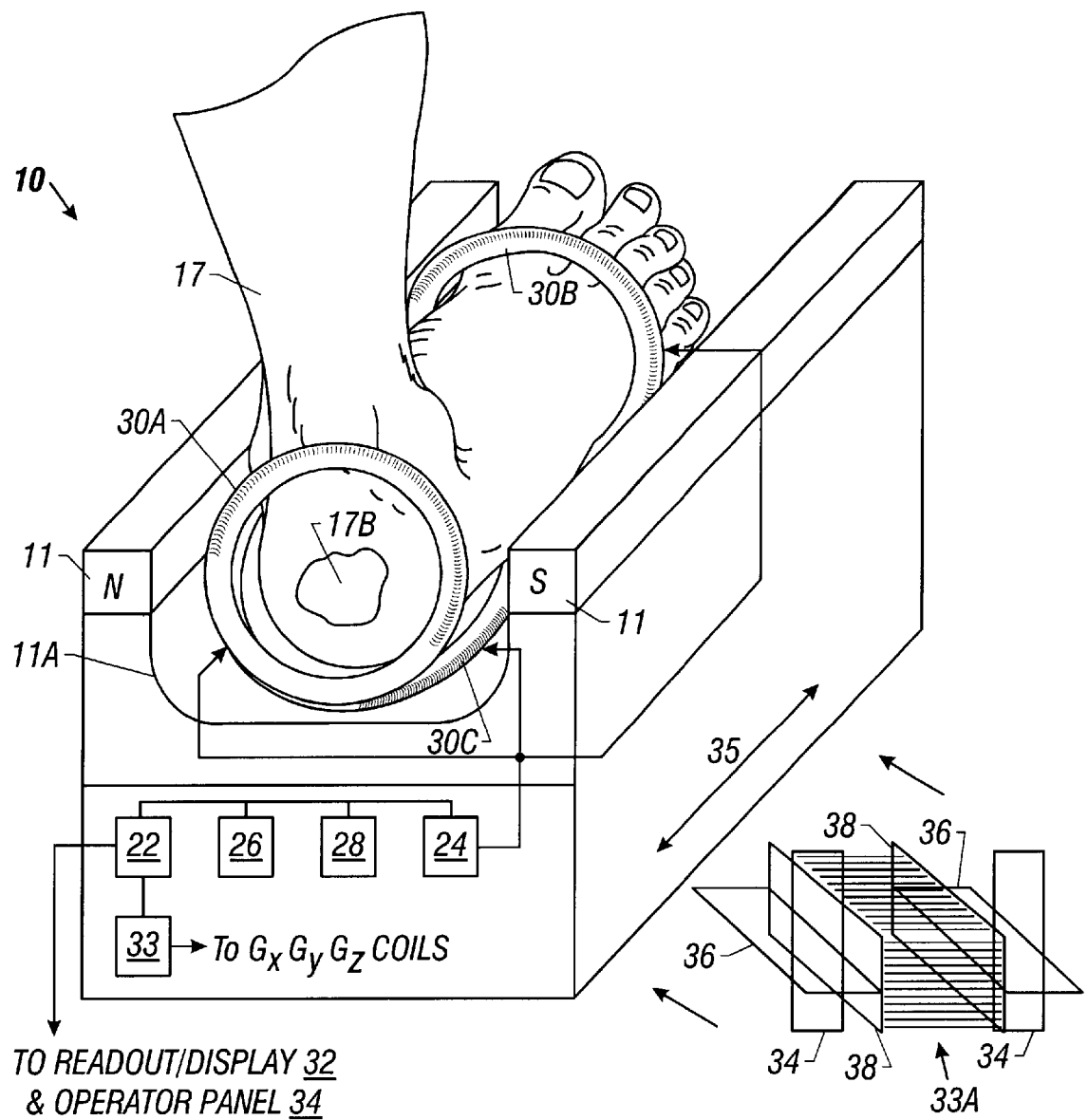
FIG. 9 shows an example of the calcaneus bone in a human foot being examined using an apparatus which can make measurements according to one example of the invention.

Another aspect of the invention is an apparatus for examining the calcaneus bone using nuclear magnetic resonance measurements. One example of a convenient-to-use NMR apparatus which can make measurements according to the invention for examining the calcaneus bone is shown generally in FIG. 9. The apparatus 10 includes a static magnetic field source 11, which in this example is a permanent magnet polarized perpendicularly to the length 35 of the apparatus 10. Note that for the magnet 11 shown in FIG. 9, the z axis, as related to the earlier description of the principle of the invention, will be oriented along the direction of polarization of the static magnetic field. The uppermost portion of the apparatus 10 preferably includes a trough 11A or other convenient receptacle to insert the body part 17 which includes the bone 17B being analyzed. In this example the body part 17 is the foot. The trough or receptacle 11A is preferably shaped to accommodate and substantially immobilize the particular body part which will be analyzed using the apparatus 10. By substantially immobilizing the body part 17, the degree of precision needed to localize the discrete volume for the NMR signal will be reduced. The trough 11A is arranged to position the foot 17 so that the length of the foot 17 is substantially parallel to the length 35 of the apparatus 10. The trough 11A in this embodiment acts as a flux closure for the magnet 11 and should therefore be made from a soft magnetic material having high saturation flux density The apparatus 10 preferably includes NMR measurement system elements such as shown in FIGS. 1 and 2 and previously explained herein. In the example apparatus 10 the RF transceiver antenna (30 in FIG. 1) is preferably shaped as two "hoops" 30A, 30B so that the foot 17 can be conveniently inserted therethrough, first by inserting the toe end of the foot through the forward hoop 30B, and then resting the heel portion of the foot within the rearward hoop 30A. The hoops 30A, 30B are connected to the network block 24 in substantially the same manner as previously explained for the RF antenna (30 in FIG. 2). As shown in FIG. 9, the hoops 30A, 30B induce an RF magnetic field substantially perpendicular to the direction of the static magnetic field induced by the magnet 11. Similarly as previously explained, the network block 24 is connected to the RF power amplifier 26 and the receiver 28, both of which are controlled by the control unit 22. The gradient power source 33 is also controlled by the control unit 22, and as previously explained is connected to gradient coils 34, 36, 38. The gradient coils 34, 36, 38 are shown in FIG. 9 to one side of the apparatus 10 for to show their relative orientation, but are included in the apparatus proximal to the magnet 11. The gradient coils 34,36,38 should be positioned on the apparatus 10 so that an open space 33A between the coils 34, 36, 38 includes the body part 17 therein. Suitable nonconductive, non-magnetic structural framework, such as can be made from plastic or the like can contain the gradient coils 34, 36, 38 in the appropriate positions relative to the body part 17 on the apparatus 10.

Alternatively, or in addition to the forward hoop 30B and rearward hoop 30B, a transceiver antenna loop 30C can be positioned as shown in FIG. 9 under the foot proximate to the calcaneus bone 17B. The RF magnetic field generated by the transceiver antenna loop 30C is substantially perpendicular to the static magnetic field and is therefore suitable for NMR measurements. In another aspect, the transceiver antenna loop 30C is substantially perpendicular to the forward 30B and rearward 30A hoops, and can therefore be used for generating and/or detecting orthogonally, or in quadrature, the NMR signals in the calcaneus bone 17A. As is known in the art, orthogonal and quadrature generating and detection of NMR signals can result in improved signal to noise ratio.

In operation, the example apparatus 10 of FIG. 9 works in substantially the same manner as the apparatus shown in FIGS. 1 and 2 and described previously herein. The apparatus measures an NMR hydrogen signal from within a selected known, discrete volume disposed within the bone of interest 17B (the calcaneus bone). Localization of the NMR signal in this example is performed as previously explained by selection of suitable gradient fields. An advantage of the apparatus 10 shown in FIG. 9 is that the calcaneus bone 17B is relatively large compared to the dimensions of the discrete volume, and the position of the foot 17 is substantially fixed by the receptacle 11A. It is therefore generally not necessary to measure the NMR signal where the discrete volume is moved to various spatial locations in order to determine whether the signal is measured entirely from within the calcaneus bone 17B. The spatial position of the discrete volume therefore can be substantially fixed using the apparatus 10 as shown in FIG. 9.

The apparatus shown in FIG. 9, in being adapted to measure properties of the calcaneus bone, may alternatively be made without the gradient coils 34, 36, 38. The shape of the static magnetic field induced by the magnet 11 is such that a relatively homogeneous field "sadlle", wherein the magnetic field has a substantially constant amplitude, will be located at a particular distance between the poles of the magnet 11. The location and size of the saddle can be selected by appropriately shaping the magnet 11. Preferably the saddle would be positioned so that substantially all of its volume is positioned within the calcaneus bone 17B. Nearly all of extraneous portions of the saddle, referred to as "wings" would also tend also to fall within the calcaneus bone 17B due to the size of the calcaneus bone, and would cause little error in the overall measurement.

The invention provides a method for quantitative magnetic resonance (QMR) analysis of a bone such as the radius, calcaneus, tibia, spine, femur and others. The results of analysis according to the invention can be used in conjunction with other clinical risk factors as an aid to physicians in diagnosis and monitoring of osteoporosis and other medical conditions which lead to reduced bone strength, and in determination of bone fracture risk.

It will be readily appreciated by persons skilled in the art that this invention is not limited to what has been particularly shown and described herein. Rather, the scope of the invention shall be limited only by the claims which follow.

What is claimed is:

1. A method for analyzing a bone, comprising:
    measuring a nuclear magnetic resonance signal corresponding to an amount of hydrogen associated with free fluid and bound water within a selected known volume of said bone, said selected known volume having a size selected so that said signal corresponds to bulk properties of said bone within said selected known volume; and
    determining a bone matrix volume from said signal.

2. The method as defined in claim 1 wherein said nuclear magnetic resonance signal comprises a steady state free precession amplitude.

3. The method as defined in claim 1 wherein said selected known volume is selected by a sensitive point technique comprising imparting a substantially homogeneous static magnetic field to said bone and superimposing mutually orthogonal oscillating gradient magnetic fields onto said static magnetic field.

4. The method as defined in claim 3 further comprising:
    superimposing bias gradient fields onto said oscillating gradient magnetic field
    observing an amplitude of said signal; and
    adjusting said bias gradient fields to move a location in space of said selected known volume until said observed amplitude reaches a localized value corresponding to a portion of interest within said bone.

5. The method as defined in claim 1 wherein said selected known volume is disposed at least partially within trabecular bone.

6. The method as defined in claim 1 wherein said selected known volume is disposed at least partially within cortical bone.

7. The method as defined in claim 1 further comprising repeating said bone matrix volume in said selected known volume at selected time intervals to observe changes in said specific bone tissue volume corresponding to a condition of said bone.

8. The method as defined in claim 1 wherein said selected known volume is disposed within the calcaneus bone.

9. The method as defined in claim 1 wherein said signal comprises contribution from free hydrogen and chemically bound hydrogen.

10. The method as defined in claim 9 wherein said nuclear magnetic resonance signal comprises components measurable by equipment having a dead time of less than about 200 microseconds.

11. A method for evaluating a condition of a bone, comprising:
    measuring a nuclear magnetic resonance signal from within a selected, known volume of said bone, said measuring localized within trabecular bone by moving said selected known volume until an amplitude of said signal reaches a value corresponding to said trabecular bone, said signal corresponding to an amount of hydrogen from within said known volume, said known volume large enough so that said signal corresponds to bulk properties within said known volume; and repeating said measuring at selected times to detect changes in a bone matrix volume calculable from said nuclear magnetic resonance signal to detect changes in said condition of said bone.

12. The method as defined in claim 11 wherein said nuclear magnetic resonance signal comprises a steady state free precession amplitude.

13. The method as defined in claim 11 wherein said selected known volume is selected by a sensitive point technique comprising imparting a substantially homogeneous static magnetic field to said bone and superimposing mutually orthogonal oscillating gradient magnetic fields onto said static magnetic field.

14. The method as defined in claim 13 wherein said localizing comprises:

superimposing bias gradient fields onto said oscillating gradient magnetic field;

observing an amplitude of said signal; and adjusting said bias gradient fields until said observed amplitude reaches a localized value corresponding to said trabecular bone.

15. The method as defined in claim 11 wherein said nuclear magnetic resonance signal comprises components measurable by equipment having a dead time of less than about 200 microseconds.

16. The method as defined in claim 1 further comprising determining a bone mineral density from one of said bone matrix volume and an amplitude of said signal.

17. A method for analyzing a bone, comprising:

measuring a nuclear magnetic resonance signal corresponding to an amount of hydrogen associated with free fluid and bound water within a selected known volume of said bone, said selected known volume having a size selected so that said signal corresponds to bulk properties of said bone within said selected known volume; and determining a bone mineral density from said signal.

18. The method as defined in claim 17 wherein said nuclear magnetic resonance signal comprises a steady state free precession amplitude.

19. The method as defined in claim 17 wherein said selected known volume is selected by a sensitive point technique comprising imparting a substantially homogeneous static magnetic field to said bone and superimposing mutually orthogonal oscillating gradient magnetic fields onto said static magnetic field.

20. The method as defined in claim 19 further comprising:

superimposing bias gradient fields onto said oscillating gradient magnetic field observing an amplitude of said signal; and adjusting said bias gradient fields to move a location in space of said selected known volume until said observed amplitude reaches a localized value corresponding to a portion of interest within said bone.

21. The method as defined in claim 17 wherein said selected known volume is disposed at least partially within trabecular bone.

22. The method as defined in claim 17 wherein said selected known volume is disposed at least partially within cortical bone.

23. The method as defined in claim 17 further comprising repeating said determining said bone mineral density in said selected known volume at selected time intervals to observe changes in said bone mineral density corresponding to a condition of said bone.

24. The method as defined in claim 23 wherein said selected known volume is disposed within the calcaneus bone.

25. The method as defined in claim 7 wherein said signal comprises contribution from free hydrogen and chemically bound hydrogen.

26. The method as defined in claim 25 wherein said nuclear magnetic resonance signal comprises components measurable by equipment having a dead time of less than about 200 microseconds.

27. An apparatus for measuring nuclear magnetic resonance properties of a calcaneus bone, comprising:

a receptacle adapted to receive and substantially immobilize a body part, said body containing said calcaneus bone therein;

a magnet for inducing a static magnetic field within said calcaneus bone;

a radio frequency pulse generator and an antenna coupled thereto positioned to induce a radio frequency magnetic field in said calcaneus bone to excite nuclear magnetic resonance therein;

a receiver and an antenna coupled thereto to detect nuclear magnetic resonance signals originating in said calcaneus bone;

means for localizing generation and detection of said nuclear magnetic resonance signals from within a selected known volume within said calcaneus bone, said signals corresponding to hydrogen associated with free fluid and bound water; and means for calculating a property of specific bone tissue within said calcaneus bone from said nuclear magnetic resonance signals.

28. The apparatus as defined in claim 27 wherein said radio frequency pulse generator and said receiver are adapted to detect steady state free precession amplitude signals.

29. The apparatus as defined in claim 27 wherein said nuclear magnetic resonance signals correspond to a number of hydrogen nuclei within a selected known volume in said calcaneus bone, and said means for calculating is adapted to determine a specific bone tissue volume within said selected known volume from said number of hydrogen nuclei.

30. The apparatus as defined in claim 27 wherein said nuclear magnetic resonance signals correspond to a number of hydrogen nuclei within a selected known volume in said calcaneus bone, and said means for calculating is adapted to determine a bone mineral density within said selected known volume from said number of hydrogen nuclei.

31. The apparatus as defined in claim 27 wherein said means for localizing comprises gradient coils disposed about said body part, said gradient coils coupled to a source of alternating current so that said static magnetic field is substantially invariant in amplitude only within said selected known volume.

32. The apparatus as defined in claim 27 wherein said receptacle comprises a trough for receiving a foot therein, said antenna for inducing said radio frequency magnetic field and said antenna for detecting said nuclear magnetic resonance signals comprise hoops disposed proximal to a toe end of said foot and a heel end of said foot, said hoops each having an axis substantially parallel to a length of said foot.

33. The apparatus as defined in claim 27 wherein said property of said bone comprises bone matrix volume.

34. The apparatus as defined in claim 27 wherein said property of said bone comprises bone mineral density.

35. The apparatus as defined in claim 27 wherein said means for localizing comprises a particularized shape for said magnet and said antenna coupled to said radio frequency pulse generator so that said nuclear magnetic signals are induced substantially only within said calcaneus bone.

* * * * *